United States Patent
Kim

(10) Patent No.: US 10,525,276 B2
(45) Date of Patent: Jan. 7, 2020

(54) LIGHT TREATMENT DEVICE USING LESION IMAGE ANALYSIS, METHOD OF DETECTING LESION POSITION THROUGH LESION IMAGE ANALYSIS FOR USE THEREIN, AND COMPUTING DEVICE-READABLE RECORDING MEDIUM HAVING THE SAME RECORDED THEREIN

(71) Applicant: ILOODA Co., Ltd., Suwon-si, Gyeonggi-do (KR)

(72) Inventor: Young Han Kim, Gunpo-si (KR)

(73) Assignee: ILOODA Co., Ltd., Suwon-si, Gyeonggi-do (KR)

( * ) Notice: Subject to any disclaimer, the term of this patent is extended or adjusted under 35 U.S.C. 154(b) by 144 days.

(21) Appl. No.: 15/542,654

(22) PCT Filed: Jan. 22, 2016

(86) PCT No.: PCT/KR2016/000739
§ 371 (c)(1),
(2) Date: Jul. 11, 2017

(87) PCT Pub. No.: WO2016/117969
PCT Pub. Date: Jul. 28, 2016

(65) Prior Publication Data
US 2018/0333589 A1    Nov. 22, 2018

(30) Foreign Application Priority Data
Jan. 23, 2015    (KR) .................. 10-2015-0011312

(51) Int. Cl.
*G06K 9/00*    (2006.01)
*A61N 5/06*    (2006.01)
(Continued)

(52) U.S. Cl.
CPC .......... *A61N 5/0616* (2013.01); *A61B 5/0077* (2013.01); *A61B 5/444* (2013.01);
(Continued)

(58) Field of Classification Search
CPC .......... A61N 5/0616; A61N 2005/0626; A61N 2007/0034; G06T 7/50; G06T 7/77;
(Continued)

(56) References Cited

U.S. PATENT DOCUMENTS 6,081,612 A * 6/2000 Gutkowicz-Krusin ...................... A61B 5/0071
382/128
6,757,415 B1 * 6/2004 Rogers ................. G06K 9/4609
382/130
(Continued)

FOREIGN PATENT DOCUMENTS

JP    09-084803 A    3/1997
KR    10-2008-0069730 A1    7/2008
(Continued)

OTHER PUBLICATIONS

International Search Report for PCT/KR2016/000739 dated Jul. 25, 2016 from Korean Intellectual Property Office.

*Primary Examiner* — Jose L Couso
(74) *Attorney, Agent, or Firm* — Revolution IP, PLLC

(57) ABSTRACT

A method of detecting a lesion position through lesion image analysis for use in a light treatment device for treating a lesion region, includes: acquiring an image of a partial region of a skin of a patient; extracting a mass, which is a predetermined region, comprising a lesion position by processing the acquired image; and detecting a lesion position through statistical analysis of a region corresponding to the extracted mass.

7 Claims, 9 Drawing Sheets

(51) Int. Cl.
*G06K 9/42* (2006.01)
*G06K 9/38* (2006.01)
*G06K 9/46* (2006.01)
*G06T 7/50* (2017.01)
*G06T 7/00* (2017.01)
*A61B 5/00* (2006.01)
*G06T 7/77* (2017.01)
*G06T 7/11* (2017.01)

(52) U.S. Cl.
CPC .............. *A61B 5/4836* (2013.01); *G06K 9/38* (2013.01); *G06K 9/42* (2013.01); *G06K 9/4642* (2013.01); *G06K 9/4647* (2013.01); *G06T 7/0012* (2013.01); *G06T 7/11* (2017.01); *G06T 7/50* (2017.01); *G06T 7/77* (2017.01); *A61B 2576/00* (2013.01); *A61N 2005/0626* (2013.01); *G06K 2209/05* (2013.01); *G06T 2207/10024* (2013.01); *G06T 2207/20021* (2013.01); *G06T 2207/20024* (2013.01); *G06T 2207/30088* (2013.01); *G06T 2207/30096* (2013.01)

(58) Field of Classification Search
CPC ......... G06T 7/0012; G06T 7/001; G06T 7/11; G06T 7/12; G06T 7/136; G06T 7/62; G06T 7/2207; G06T 7/20024; G06T 7/30096; G06T 7/30088; G06T 7/30004; G06T 7/10024; G06T 7/20192; G06T 7/20212; G06T 7/30024; G06T 7/30068; G06T 2210/41; A61B 5/0077; A61B 5/4836; A61B 5/0033; A61B 5/0059; A61B 5/7264; A61B 5/103; A61B 5/441–445; A61B 5/448; A61B 5/4312; A61B 5/4842; A61B 5/1032; A61B 2018/0047; A61B 2018/00476; A61B 2018/00577; A61B 2017/00747; A61B 2017/00752; A61B 2576/00; G06K 9/38; G06K 9/42; G06K 9/4642; G06K 9/4647; G06K 9/62–6298; G06K 9/68; G06K 9/70; G06K 9/72; G06K 9/78; G06K 9/80; G06K 9/3233; G06K 9/00127; G06K 9/00147; G06K 9/00362; G06K 2209/05; G06F 19/321; G16H 50/20; G16H 50/70

See application file for complete search history.

(56) References Cited

U.S. PATENT DOCUMENTS

| | | | | |
|---|---|---|---|---|
| 7,298,877 | B1* | 11/2007 | Collins | G01N 23/04 378/1 |
| 8,503,742 | B2* | 8/2013 | Dewaele | G06T 7/0012 382/128 |
| 2004/0258285 | A1* | 12/2004 | Hansen | G06T 7/0012 382/128 |
| 2004/0264749 | A1* | 12/2004 | Skladnev | A61B 5/0059 382/128 |
| 2004/0267102 | A1* | 12/2004 | Skladnev | A61B 5/442 600/315 |
| 2005/0228264 | A1* | 10/2005 | Grichnik | A61B 5/0059 600/411 |
| 2009/0209833 | A1* | 8/2009 | Waagen | G06T 7/0016 600/306 |
| 2009/0279760 | A1* | 11/2009 | Bergman | G06T 7/0012 382/128 |
| 2010/0158330 | A1* | 6/2010 | Guissin | G06K 9/00369 382/128 |
| 2014/0034159 | A1 | 2/2014 | Myrhum, Jr. | |
| 2014/0036054 | A1* | 2/2014 | Zouridakis | G06T 7/0012 348/77 |
| 2015/0025343 | A1* | 1/2015 | Gareau | A61B 5/6898 600/328 |
| 2015/0374309 | A1* | 12/2015 | Farkas | G01N 21/21 600/473 |
| 2016/0007856 | A1* | 1/2016 | Ishihara | G02B 23/2469 600/476 |
| 2017/0032521 | A1* | 2/2017 | Kubo | A61N 5/06 |
| 2017/0231550 | A1* | 8/2017 | Do | G06T 7/11 382/128 |
| 2017/0287134 | A1* | 10/2017 | Abedini | G06K 9/622 |
| 2018/0000406 | A1* | 1/2018 | Wang | A61B 5/0075 |
| 2018/0054565 | A1* | 2/2018 | Smith | G03B 17/565 |
| 2018/0103892 | A1* | 4/2018 | Kaur | A61B 5/444 |
| 2018/0122065 | A1* | 5/2018 | Abedini | G06T 7/0012 |
| 2018/0218496 | A1* | 8/2018 | Sinai | G06T 7/0012 |
| 2018/0333105 | A1* | 11/2018 | Hayat | A61B 5/7264 |
| 2019/0133514 | A1* | 5/2019 | Gareau | A61B 5/6898 |
| 2019/0147594 | A1* | 5/2019 | Abedini | G06T 7/0012 |

FOREIGN PATENT DOCUMENTS

| | | |
|---|---|---|
| KR | 10-2009-0059667 A | 6/2009 |
| KR | 10-1197863 B1 | 11/2012 |
| KR | 10-1244434 B1 | 3/2013 |
| KR | 10-2013-0057443 A | 5/2013 |
| KR | 10-2014-0018748 A | 2/2014 |
| KR | 10-2014-0094975 A | 7/2014 |

* cited by examiner

[FIG. 1]
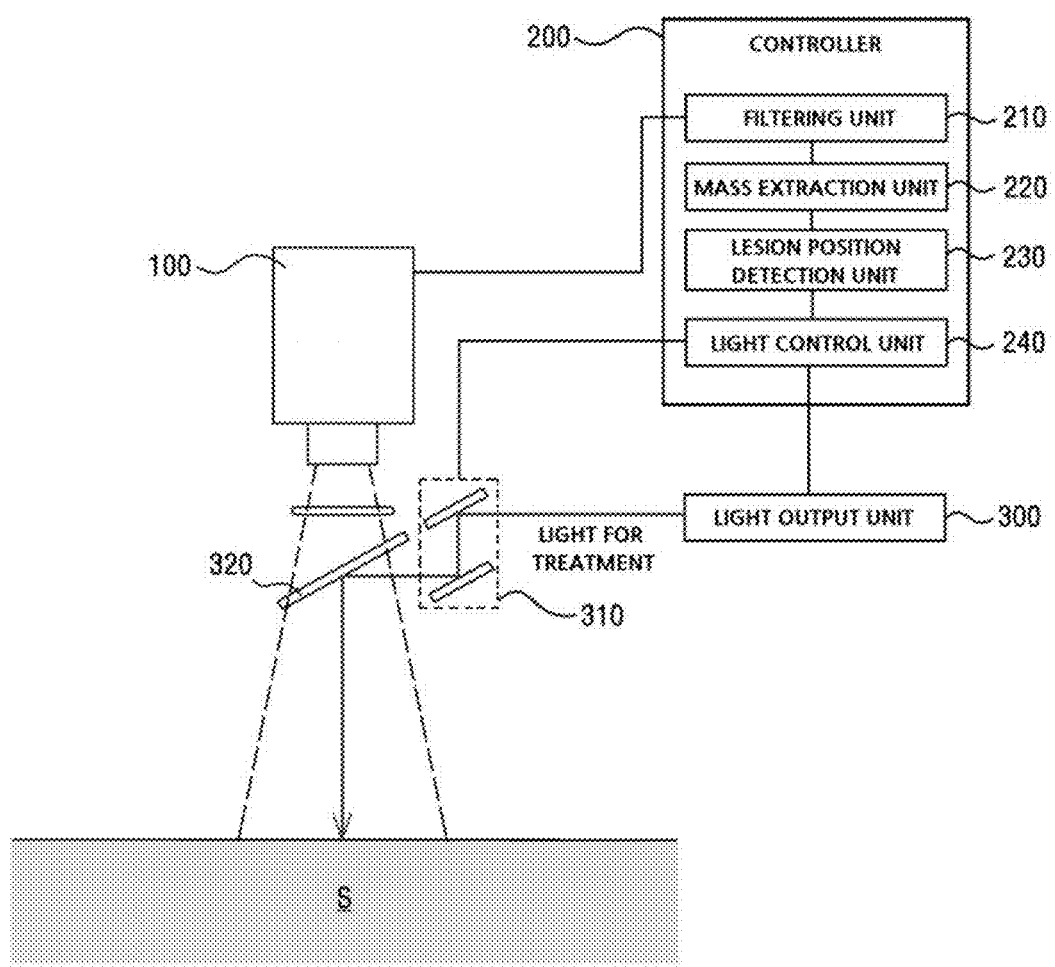

[FIG. 2]
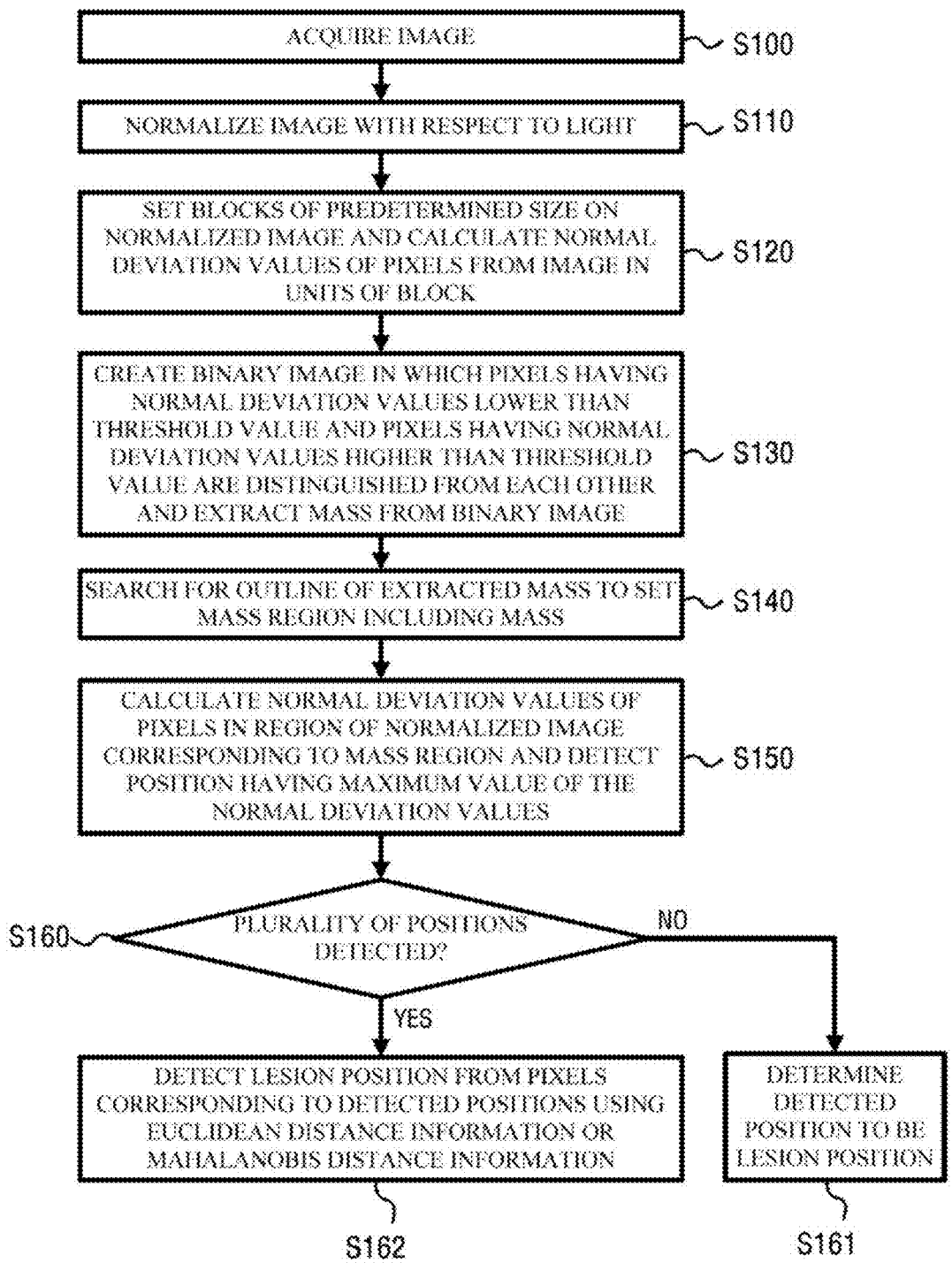

【FIG. 3】
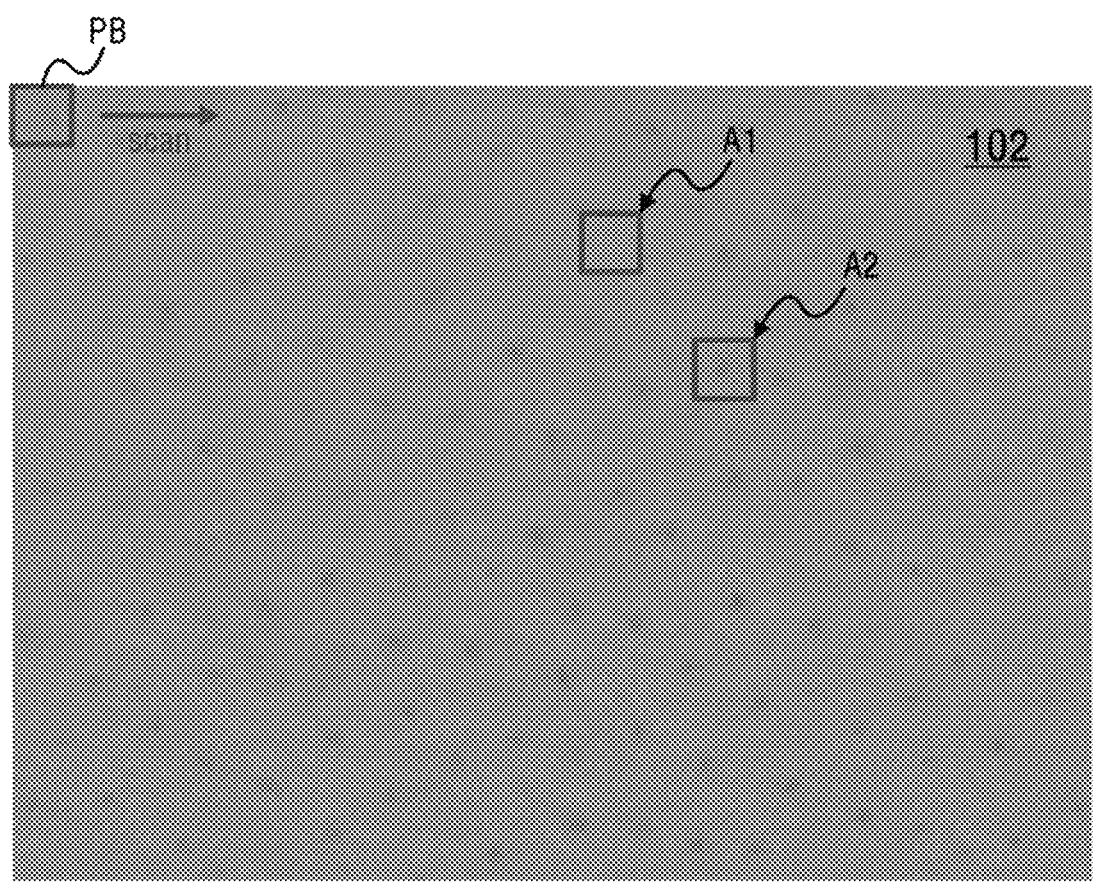

[FIG. 4]
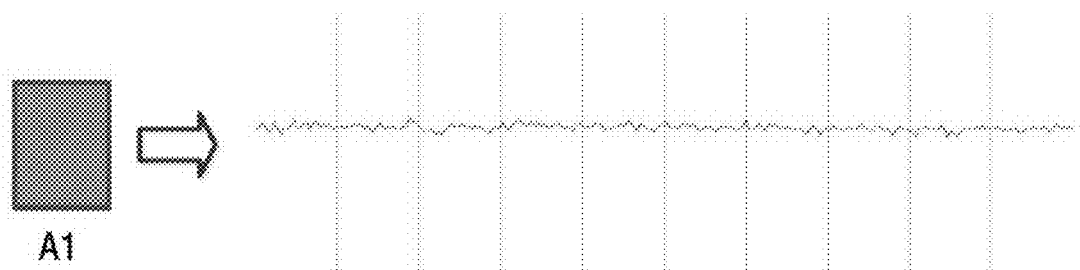
(a)
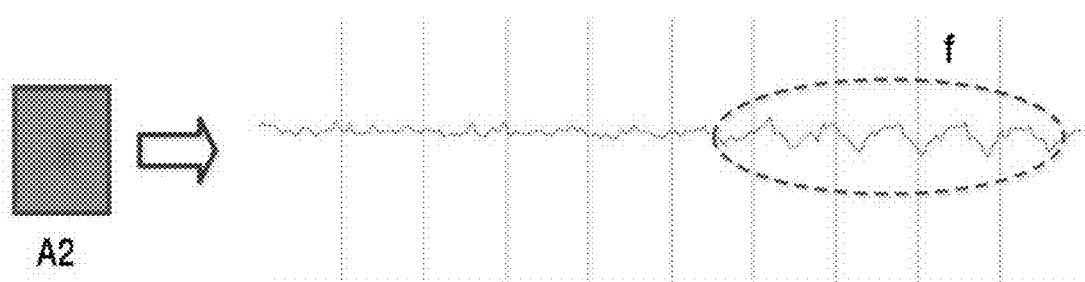
(b)

【FIG. 5】
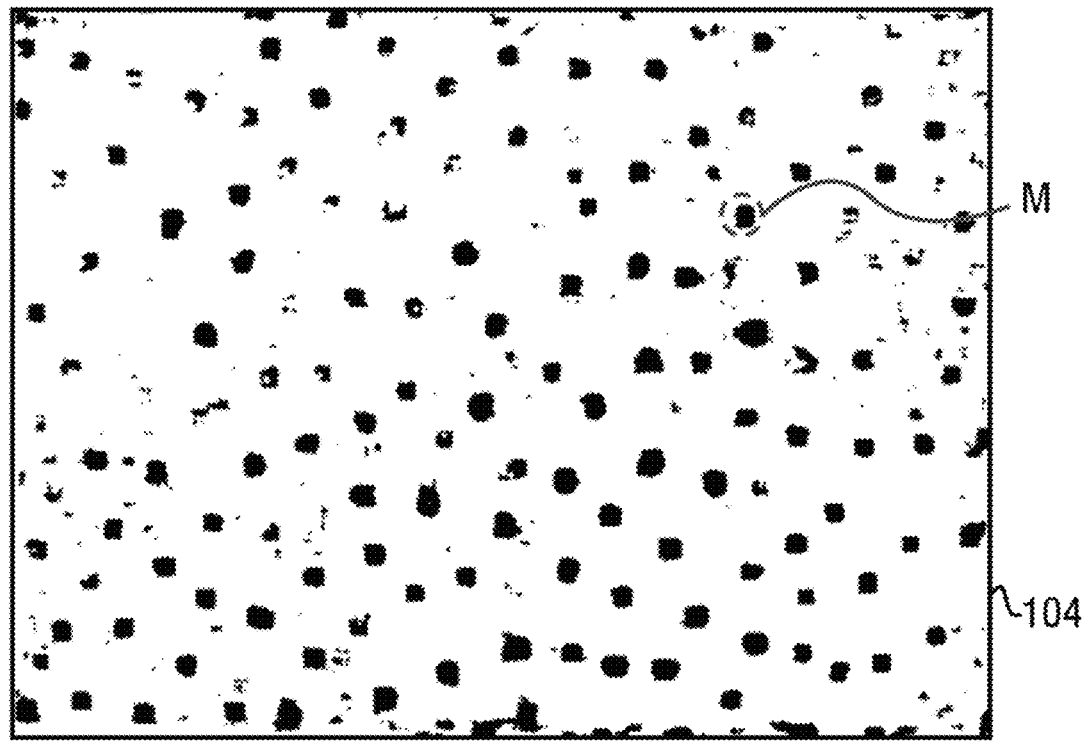
(a)
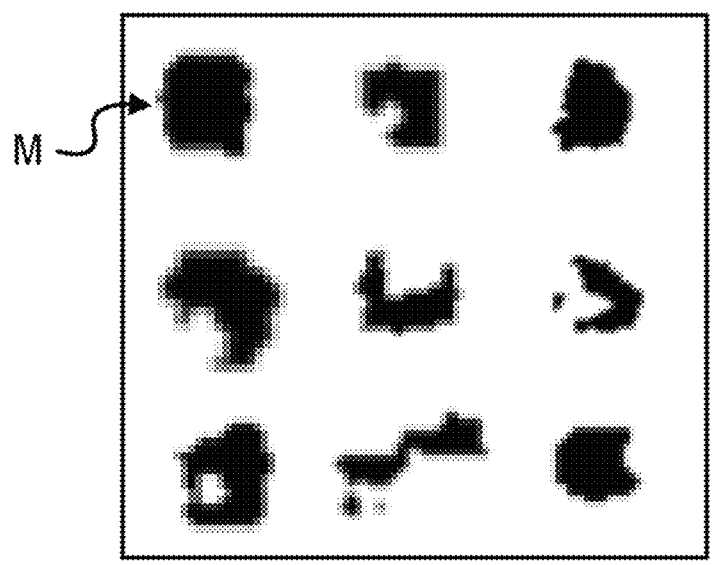
(b)

【FIG. 6】
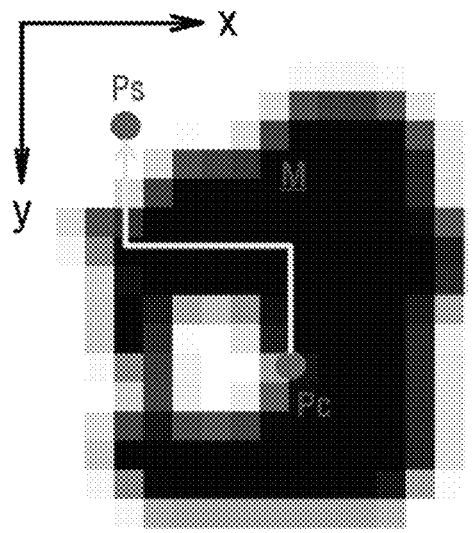
(a)
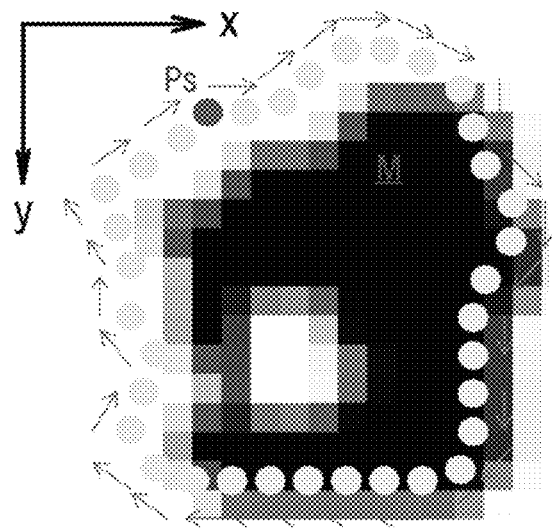
(b)
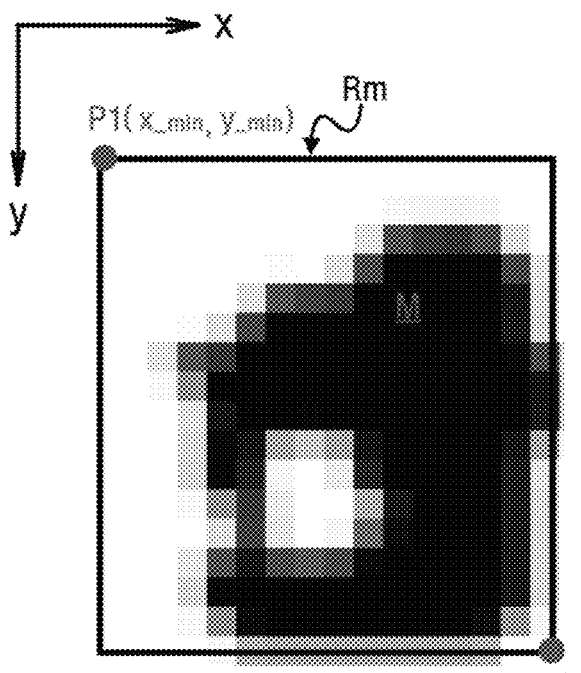
(c)

[FIG. 7]
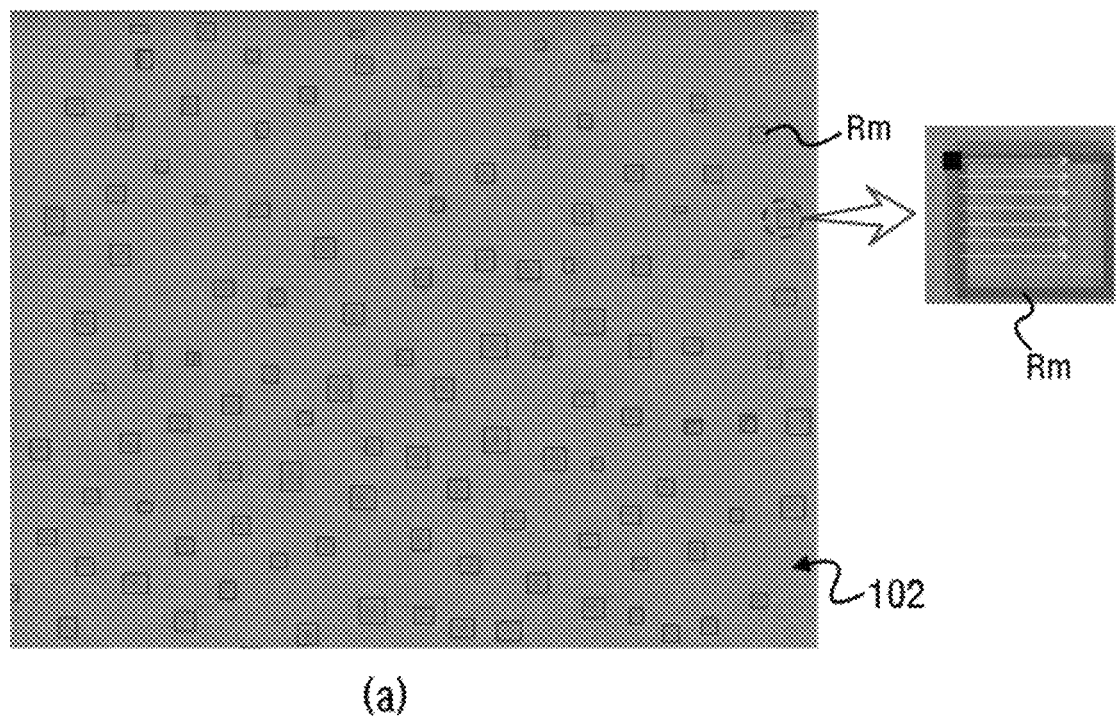
(a)
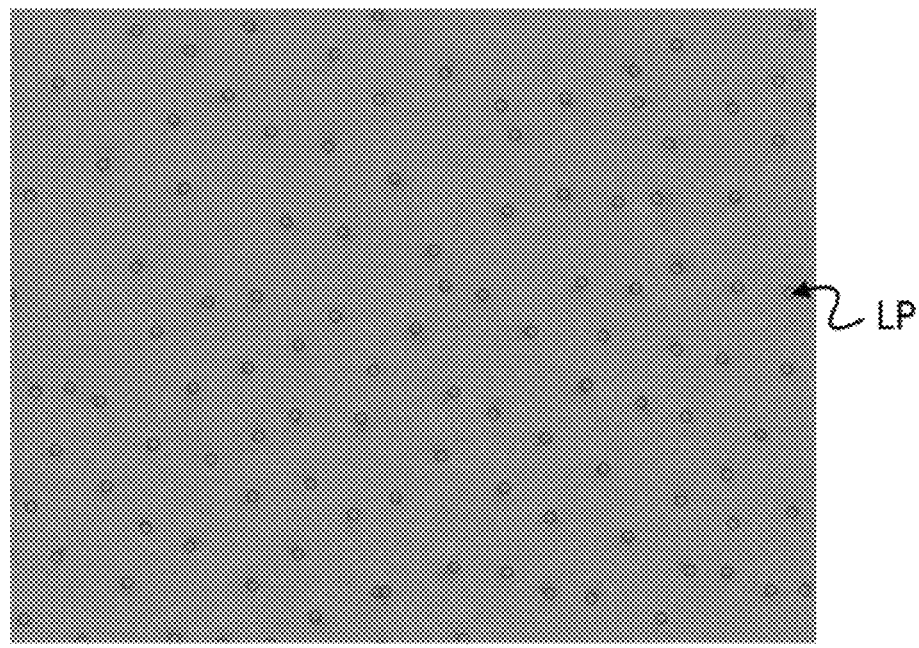
(b)

[FIG. 8]
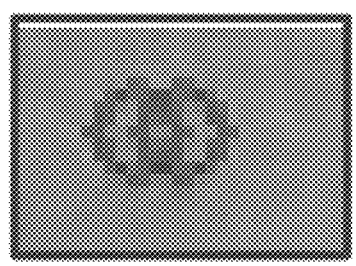
(a)
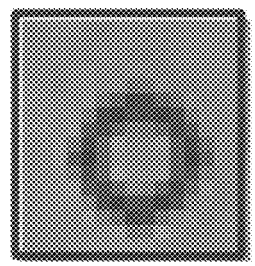
(b)
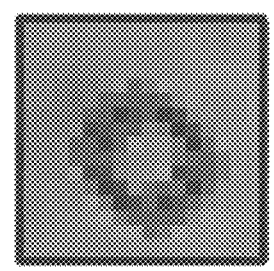
(c)
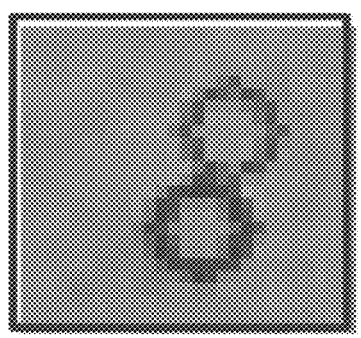
(d)
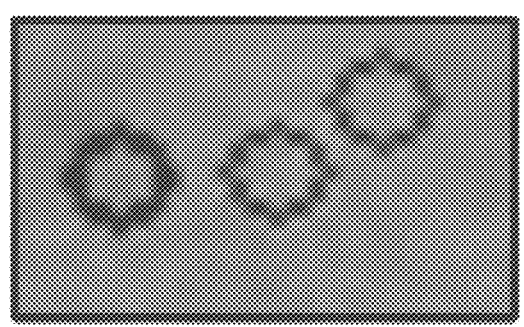
(e)

[FIG. 9]
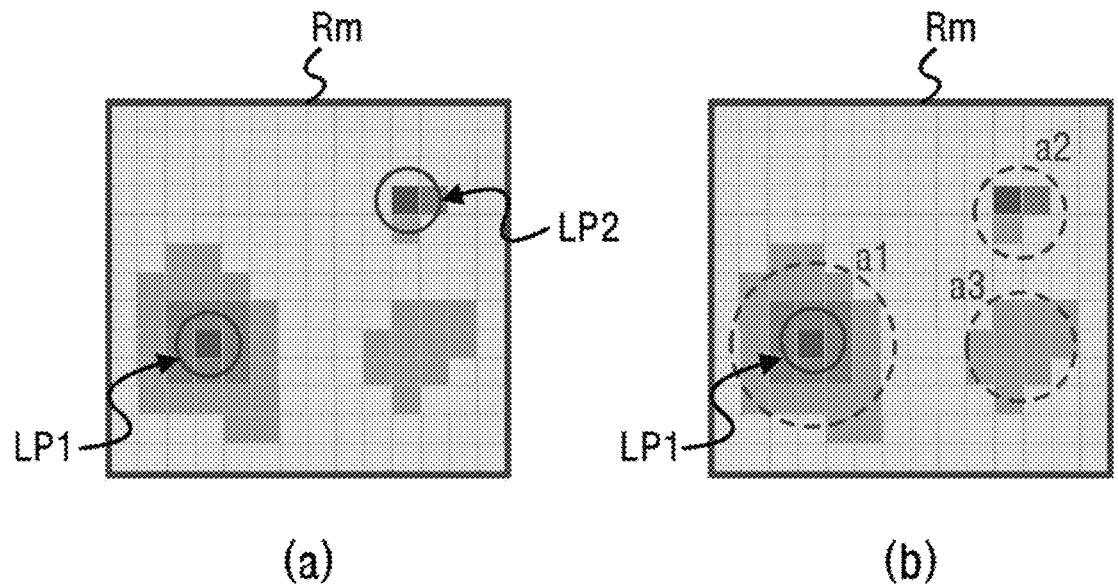
[FIG. 10]
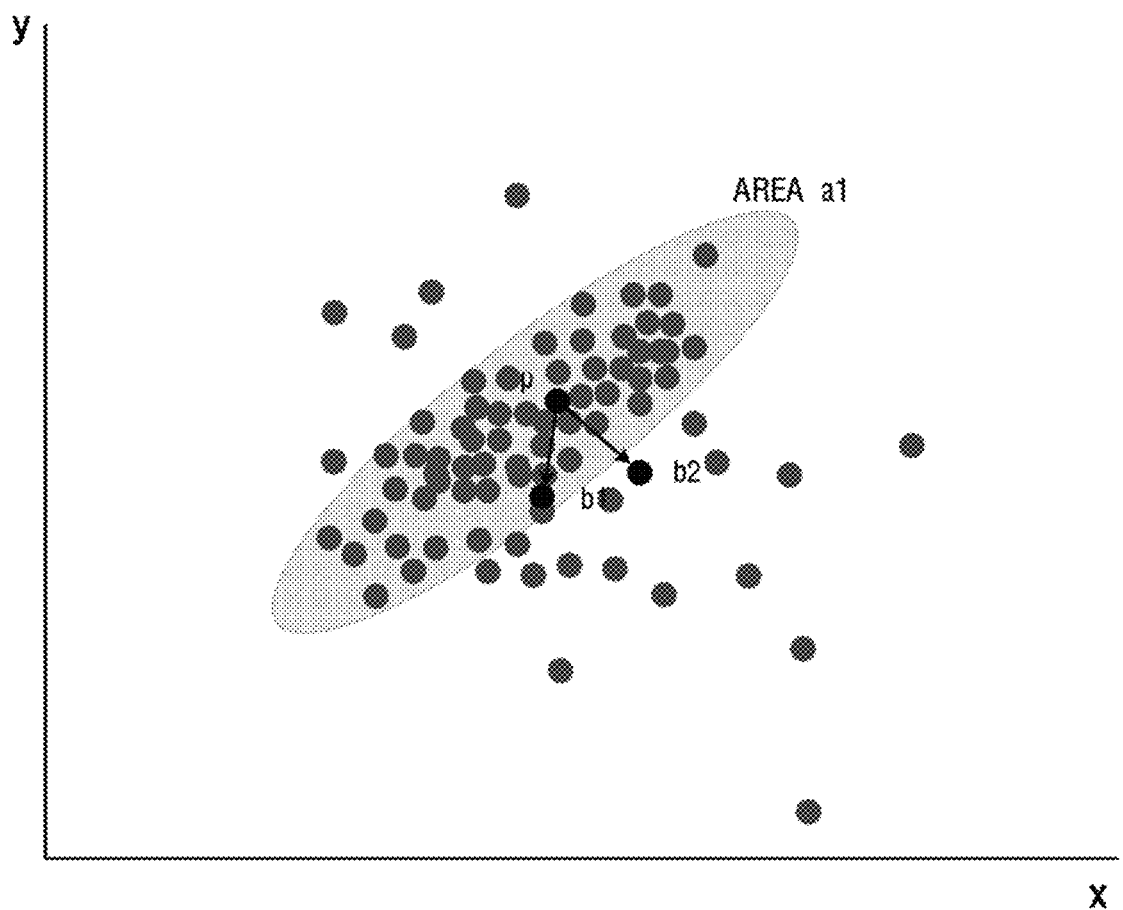

LIGHT TREATMENT DEVICE USING LESION IMAGE ANALYSIS, METHOD OF DETECTING LESION POSITION THROUGH LESION IMAGE ANALYSIS FOR USE THEREIN, AND COMPUTING DEVICE-READABLE RECORDING MEDIUM HAVING THE SAME RECORDED THEREIN

CROSS REFERENCE TO PRIOR APPLICATIONS

This application is a National Stage Application of PCT International Patent Application No. PCT/KR2016/000739 filed on Jan. 22, 2016, under 35 U.S.C. § 371, which claims priority to Korean Patent Application No. 10-2015-0011312 filed on Jan. 23, 2015, which are all hereby incorporated by reference in their entirety.

TECHNICAL FIELD

The present invention relates to a light treatment device using lesion image analysis that is capable of analyzing an image of the skin of a patient and automatically removing hairs, freckles, blemishes, flecks, etc. and treating various kinds of skin diseases using a specific kind of light, such as a laser, and a method of detecting a lesion position through lesion image analysis for use therein.

BACKGROUND ART

In general, there have been widely used treatment devices that remove color lesions, such as freckles, blemishes, and flecks, from the skin of a patient, remove hairs, and treat various kinds of skin diseases using light.

A skin treatment device using light radiates light of a single wavelength or mixed wavelengths to the skin of a patient to treat various kinds of skin diseases. For example, the skin treatment device radiates light of a specific wavelength to the skin of a patient to permanently remove hairs, to widen capillary vessels in the face, or to treat skin diseases including color diseases, such as flushing of the face, freckles, and flecks.

Light for treatment used to treat such skin diseases is output from a laser light source of a specific wavelength or a light emitting diode.

Technologies related to the present invention are disclosed in Japanese Patent Application Publication No. H09-084803, Korean Registered Patent No. 10-1244434, and Korean Patent Application Publication No. 10-2009-0059667.

A representative example of the light treatment device is a laser hair remover, which radiates laser to pores in the skin of a patient to burn the pores. Conventionally, a high-output laser beam having a large area is radiated in order to remove a large number of hairs within a short period of time.

In this type of hair removal using a laser, however, serious side effects, such as skin burns and spots, may be caused. In addition, this type of hair removal using a laser may not be used for all races having different skin colors, such as the black race and the white race.

DISCLOSURE

Technical Problem

It is an object of the present invention to provide a method of treating a lesion region using light in a manner totally different from a conventional manner, in which light for treatment is radiated to a large area of the skin of a patient having a lesion region in order to treat a patch of lesion regions together, and particularly to provide a light treatment device using lesion image analysis, a method of detecting a lesion position through lesion image analysis for use therein, and a computing device-readable recording medium having the same recorded therein which are capable of acquiring an image of a skin region of a patient, analyzing the acquired image to precisely detect a position at which a lesion is present, and radiating light for treatment to the detected lesion position to treat only the lesion position, thereby preventing the occurrence of side effects, such as skin burns and spots, and which can be used for all races having different skin colors.

Technical Solution

In accordance with one aspect of the present invention, the above and other objects can be accomplished by the provision of a method of detecting a lesion position through lesion image analysis for use in a light treatment device for treating a lesion region, the method including acquiring an image of a partial region of the skin of a patient, extracting a mass, which is a predetermined region, including a lesion position by processing the acquired image, and detecting a lesion position through statistical analysis of a region corresponding to the extracted mass.

The step of extracting the mass may include normalizing the acquired image based on a predetermined parameter such that the mass is distinguished from surroundings in the image.

In addition, the step of extracting the mass may include creating a binary image in which the mass is distinguished from surroundings using normal deviation values of pixels in the image to extract the mass.

In addition, the step of extracting the mass may include filtering the acquired image to normalize the image with respect to light based on a predetermined parameter, setting a plurality of blocks of a predetermined size in the filtered image, and scanning the raw image and calculating normal deviation values of pixels in units of a block, and setting a threshold value for the normal deviation values in advance and creating a binary image in which pixels in each block having normal deviation values lower than the threshold value and pixels in each block having normal deviation values higher than the threshold value are distinguished from each other to extract the mass.

The step of detecting the lesion position may include setting a mass region including the extracted mass in the image, detecting the minimum brightness value of each pixel in a region of the acquired image or a filtered image of the acquired image corresponding to the set mass region, and detecting a pixel group having a predetermined range of brightness values based on the detected minimum brightness value.

In addition, the step of detecting the lesion position may include setting a mass region including the extracted mass in the image and detecting a position having a highest deviation with respect to an average of brightness values of all pixels in a region of the acquired image or a filtered image of the acquired image corresponding to the set mass region.

In addition, the step of detecting the lesion position may include setting a mass region including the extracted mass in the image, calculating a normal deviation value of each pixel in a region of the acquired image or a filtered image of the acquired image corresponding to the set mass region, and detecting a position at which the calculated normal deviation value is the maximum value.

In addition, the step of detecting the lesion position may include, in the case in which a plurality of pixel groups is detected, detecting one of the pixel groups having the highest deviation with respect to the average of brightness values of all pixels and detecting a position in the detected pixel group at which the brightness value of the pixel is the minimum as the lesion position.

In addition, the step of detecting the lesion position may include setting a mass region including the extracted mass in the image, calculating a normal deviation value of each pixel in a region of the acquired image or a filtered image of the acquired image corresponding to the set mass region, detecting a position at which the calculated normal deviation value is the maximum value, and detecting the lesion position through different processes in the case in which a single position is detected and in the case in which a plurality of positions is detected The method may include, in the case in which the plurality of positions is detected, calculating the Euclidean distance between points at all of the detected positions, and in the case in which the calculated Euclidean distance is less than a predetermined value, selecting one of the detected positions and determining the selected position to be the lesion position.

In addition, the method may include, in the case in which the plurality of positions is detected, calculating the Euclidean distance between points at all of the detected positions, and in the case in which the calculated Euclidean distance is greater than a predetermined value, detecting pixels having normal deviation values higher than a threshold value set in advance for the normal deviation value calculated at the step of calculating the normal deviation value of each pixel, and calculating the Euclidean distance between the detected pixels to detect a pixel group having pixels gathered in a predetermined value or lower and detecting a position in the detected pixel group at which the normal deviation value is the maximum as the lesion position.

In addition, the step of detecting the lesion position may include setting a mass region including the extracted mass in the image, detecting the minimum brightness value of each pixel in a region of the acquired image or a filtered image of the acquired image corresponding to the set mass region, detecting pixels having a predetermined range of brightness values based on the detected minimum brightness value, calculating a covariance for positions of the detected pixels and calculating the Mahalanobis distance between points based on the calculated covariance, and detecting a pixel group having the calculated Mahalanobis distance less than a predetermined value as the lesion position.

In addition, the step of detecting the lesion position may include setting a mass region including the extracted mass in the image, calculating a normal deviation value of each pixel in a region of the acquired image or a filtered image of the acquired image corresponding to the set mass region, detecting pixels having normal deviation values higher than a threshold value set in advance for the calculated normal deviation value, calculating a covariance for positions of the detected pixels and calculating the Mahalanobis distance between points based on the calculated covariance, and detecting a pixel group having the calculated Mahalanobis distance less than a predetermined value as the lesion position.

In accordance with another aspect of the present invention, there is provided a computing device-readable recording medium having the method of detecting the lesion position as described above recorded therein.

In accordance with a further aspect of the present invention, there is provided a light treatment device for treating a lesion region, configured to detect a lesion position through lesion image analysis and radiate light to the detected lesion position, the light treatment device including an image acquisition unit for acquiring an image of a partial region of the skin of a patient, a controller for extracting a mass, which is a predetermined region, including a lesion position by processing the acquired image and detecting a lesion position through statistical analysis of a region corresponding to the extracted mass, a light output unit configured to output light for treatment to the skin of the patient under the control of the controller, and a light coordinate adjustment unit for adjusting the coordinates of the light for treatment output by the light output unit under the control of the controller such that the light for treatment is radiated to the lesion position detected by the controller.

The controller may include a mass extraction unit for creating a binary image in which the mass is distinguished from its surroundings using normal deviation values of pixels in the image to extract the mass and a lesion position detection unit for setting a mass region including the mass extracted by the mass extraction unit, calculating a normal deviation value of each pixel in a region corresponding to the set mass region, and detecting a position at which the calculated normal deviation value is the maximum value as the lesion position.

In addition, the controller may include a filtering unit for normalizing the acquired image with respect to light based on a predetermined parameter, a mass extraction unit for setting a plurality of blocks of a predetermined size on the normalized image, calculating normal deviation values of pixels in units of a block, and creating a binary image in which pixels in each block having normal deviation values lower than a threshold value and pixels in each block having normal deviation values higher than the threshold value are distinguished from each other to extract the mass, and a lesion position detection unit for setting a mass region including the mass extracted by the mass extraction unit, calculating a normal deviation value of each pixel in a region of the normalized image corresponding to the set mass region, and detecting a position at which the normal deviation value is the maximum value as the lesion position or for detecting positions having normal deviation values higher than a threshold value set in advance for the calculated normal deviation value, calculating the Euclidean distance between pixels of the detected positions, and detecting one of the positions satisfying a predetermined condition using the calculated Euclidean distance as the lesion position.

Advantageous Effects

A light treatment device using lesion image analysis according to the present invention, a method of detecting a lesion position through lesion image analysis for use therein, and a computing device-readable recording medium having the same recorded therein are capable of acquiring an image of a skin region of a patient, analyzing the acquired image to precisely detect a position at which a lesion is present, and radiating light for treatment to the detected lesion position to treat only the lesion position, thereby preventing the occurrence of side effects, such as skin burns and spots, and can be used for all races having different skin colors.

DESCRIPTION OF DRAWINGS

FIG. 1 is a block diagram showing the construction of a light treatment device using lesion image analysis according to an embodiment of the present invention;

FIG. 2 is a flowchart showing a lesion position detection method using lesion image analysis according to an embodiment of the present invention;

FIG. 3 is a view showing an example of an image acquired by an image acquisition unit of the present invention and normalized with respect to light;

FIG. 4 is a view showing a change in the normal deviation values for each of area A1 and area A2 shown in FIG. 3;

FIG. 5 is a view showing a process of creating a binary image from the normalized image shown in FIG. 3 to extract a mass;

FIG. 6 is a view showing a process of setting a mass region for the mass shown in FIG. 5;

FIG. 7 shows a view (a) showing an image obtained by displaying the mass regions set as shown in FIG. 6 in the raw image shown in FIG. 3 and a view (b) showing an image having lesion positions detected from the mass regions;

FIG. 8 is a view showing the case in which a plurality of positions has been detected in the mass regions in accordance with the lesion position detection method according to the embodiment of the present invention; and FIGS. 9 and 10 are views illustrating a process of detecting lesion positions in accordance with the lesion position detection method according to the embodiment of the present invention in the case in which the positions have been detected as shown in FIG. 8.

BEST MODE

Hereinafter, a light treatment device using lesion image analysis according to the present invention and a method of detecting a lesion position through lesion image analysis for use therein will be described in detail with reference to the accompanying drawings.

First, the construction of a light treatment device using lesion image analysis according to an embodiment of the present invention will be described with reference to FIG. 1. FIG. 1 is a block diagram showing the construction of a light treatment device using lesion image analysis according to an embodiment of the present invention.

As shown in FIG. 1, the light treatment device using lesion image analysis according to the embodiment of the present invention includes an image acquisition unit 100, a controller 200, a light output unit 300, and a light coordinate adjustment unit 310.

The image acquisition unit 100 may be realized by a camera or a camera module for acquiring an image of the skin S of a patient. The image acquisition unit 100 may be further provided with a separate lighting device for emitting light to the skin S.

For example, the lighting device may emit light of a specific wavelength (e.g. infrared rays) to the skin S such that blood vessels can be clearly seen through the skin S. In an image acquired by the image acquisition unit 100 under such a light condition, therefore, a blood vessel may be clearly visible at the surface of the skin.

An image of a lesion region acquired by the image acquisition unit 100 is transmitted to the controller 200. The controller 200 analyzes the image of the lesion region to precisely detect the position of the lesion region from the image of the lesion region, and perform control such that light for treatment is precisely emitted to the detected position of the lesion region.

Meanwhile, as shown in FIG. 1, a selective transmission mirror 320 may be provided within the angle of view of the image acquisition unit 100. The selective transmission mirror 320 may be installed in an image-taking region of the image acquisition unit 100 to transmit light incident in the image acquisition unit 100 such that the image acquisition unit 100 can acquire an image of the skin and to reflect light for treatment such that the light for treatment can be radiated to the lesion region of the skin. The selective transmission mirror 320 is a well-known element, and therefore a detailed description thereof will be omitted.

The light output unit 300 is an element for outputting light for treatment under the control of the controller 200.

The light coordinate adjustment unit 310 appropriately reflects light for treatment output from the light output unit 300 to adjust the position to which the light for treatment is radiated such that the light for treatment can be precisely radiated to the coordinate position of a lesion region on the skin S of the patient.

The light coordinate adjustment unit 310 is configured to adjust the x coordinate position and the y coordinate position on an x-y coordinate plane to which light for treatment is radiated, on the assumption that the region of the skin S to be treated is defined by the x-y coordinate plane. For example, as shown in FIG. 1, the x coordinate position and the y coordinate position to which light for treatment is radiated may be adjusted using two reflection mirrors, and a light control unit 240 of the controller 200 may control the angle of the two reflection mirrors to adjust the position to which light for treatment is radiated.

Meanwhile, the controller 200 process and analyzes the image of the lesion region received from the image acquisition unit 100 to precisely calculate information about coordinates of the lesion region, and controls the light coordinate adjustment unit 310 such that light for treatment can be precisely radiated to the calculated coordinate positions.

More specifically, the controller 200 may be divided into several elements depending on the function thereof. As shown in FIG. 1, the controller 200 may include a filtering unit 210, a mass extraction unit 220, a lesion position detection unit 230, and a light control unit 240.

The filtering unit 210 normalizes the image, acquired by the image acquisition unit 100 and received from the image acquisition unit 100, with respect to light based on predetermined parameters.

That is, light in the image acquired by the image acquisition unit 100 is non-uniform, with the result that it is not proper to detect a lesion region from the image itself. For example, lesion regions in an image acquired in the state in which light is uniform have similar pixel information; whereas lesion regions in an image acquired in the state in which light is non-uniform may have great differences in pixel information, or there may be little differences in pixel information between lesion regions and the surroundings thereof.

In order to precisely detect the lesion regions from the image acquired by the image acquisition unit 100, therefore, it is necessary to remove the effects of non-uniform light from the acquired image. To this end, the filtering unit 210 is provided.

Meanwhile, the mass extraction unit 220 processes the image, normalized with respect to light by the filtering unit 210, through predetermined image processing to extract a region in which there is a high possibility of a lesion position being found (hereinafter, referred to as a "mass"). A method of extracting a mass from an image using the mass extraction unit 220 will be described below in more detail.

Meanwhile, the lesion position detection unit 230 analyzes data (i.e. pixels) within a predetermined region corresponding to the mass extracted by the mass extraction unit 220 from the image, normalized with respect to light by the filtering unit 210, to precisely detect a lesion position. The function of the lesion position detection unit 230 will be described below in more detail.

Meanwhile, the light control unit 240 is an element that controls the light output unit 300 and the light coordinate adjustment unit 310. When it is necessary to output light for treatment (for example, when an operator pushes an output button), the light control unit 240 performs control such that the light output unit 300 radiates light for treatment. In addition, when coordinate information of the lesion position is calculated by the lesion position detection unit 230, the light control unit 240 controls the light coordinate adjustment unit 310 such that the light for treatment is precisely radiated to the calculated coordinate positions (for example, the angles of the two reflection mirrors of the light coordinate adjustment unit are adjusted).

Hereinafter, a lesion position detection method using lesion image analysis according to an embodiment of the present invention will be described with reference to the flowchart shown in FIG. 2.

The lesion position detection method performed according to the flowchart shown in FIG. 2 is performed by the image acquisition unit and the controller of the light treatment device according to the embodiment of the present invention shown in FIG. 1. Specifically, the lesion position detection method is performed by the image acquisition unit 100, the filtering unit 210, the mass extraction unit 220, and the lesion position detection unit 230.

First, when an image of a skin of a patient having a lesion is acquired by the image acquisition unit (S100), the image acquisition unit transmits the acquired image to the controller.

The filtering unit of the controller normalizes the received image with respect to light in order to remove the effects of non-uniform light from the image (S110). Hereinafter, the image normalized with respect to light will be referred to as a "raw image."

The mass extraction unit of the controller sets a plurality of blocks of a predetermined size in the raw image, and scans the raw image to calculate normal deviation values of brightness of pixels in units of a block (S120).

Subsequently, a binary image is created such that pixels having normal deviation values lower than a predetermined threshold value have a brightness value of 0 and pixels having normal deviation values higher than the threshold value have a specific brightness value, i.e. such that pixels are divided into pixels having high normal deviation and pixels having low normal deviation on the basis of the threshold value (S130).

That is, a binary image is created such that pixels having normal deviation values lower than the threshold value are seen as white and pixels having normal deviation values higher than the threshold value are seen as black.

In the created binary image, a region including a lesion position is seen as a lump, which will be referred to as a "mass." The mass extraction unit creates the binary image such that the mass clearly appears in the binary image. That is, the mass is extracted from the binary image, which is created from the raw image (S130).

Subsequently, the mass extraction unit searches for the outline of the extracted mass to set a "mass region" including the mass (S140). Steps S120 to S140 will be described below in more detail.

Meanwhile, after the mass is extracted from the binary image and the mass region is set, as described above, the lesion position detection unit analyzes pixels in the region of the raw image corresponding to the mass region to detect the lesion position.

The pixels in the mass region may be analyzed to detect the lesion position using various methods. In one example, the lesion position may be detected using normal deviation values of pixels in an image.

That is, the lesion position detection unit calculates normal deviation values of pixels in the region of the raw image corresponding to the mass region and detects a position having the maximum value of the normal deviation values (S150). In the case in which there is only a single position having the maximum value of the detected normal deviation values, the position is determined to be a lesion position (S161).

Here, the term "position" may mean one pixel or two or more pixels.

In the case in which there is a plurality of positions having the maximum value of the normal deviation values of the pixels in the region of the raw image corresponding to the mass region (S160), Euclidean distance information or Mahalanobis distance information is calculated from the pixels corresponding to the detected positions, one of the positions is selected based on a specific condition using the calculated information, and the selected position is detected as a lesion position (S162).

Detection of the lesion position will be described below in more detail with reference to FIGS. 3 to 10. FIGS. 3 to 10 show the case in which a pore of the skin is detected as a lesion position.

However, the present invention also includes a method of detecting a lesion position based on freckles, blemishes, flecks, or various kinds of skin diseases, in addition to pores. The method of detecting a lesion position in such a manner may be performed according to the same principle as a method of detecting a pore, a description of which will follow.

FIG. 3 is a view showing an example of an image of a skin of a patient acquired by the image acquisition unit of the present invention and normalized with respect to light by the filtering unit, i.e. a raw image.

The controller of the light treatment device according to the present invention finds a pore that can be recognized with the naked eye from the raw image, denoted by reference numeral 102, shown in FIG. 3 using the method performed according to the flowchart shown in FIG. 2.

In nearly all cases, a lesion region, such as a pore, in an image appears as a group of pixels having pixel values (i.e. brightness values) different from those of the surroundings.

The mass extraction unit of the controller scans the entirety of the raw image 102 shown in FIG. 3 in units of a block PB having a predetermined size. The size of the block PB may be the size of one pixel or the size of a plurality of pixels.

For example, in FIG. 3, normal deviation values of pixels in the block PB are calculated based on the average value of the pixels in the block PB while the block PB is moved from the left end of the image 102 in the direction indicated by the arrow.

While scanning is performed in units of a block PB, a lesion region may or may not be included in the block PB.

In FIG. 3, area A1 is an area in which a lesion region is not included in the block, and area A2 is an area in which a lesion region is included in the block.

A change in the normal deviation values of the pixels in the block when a lesion region is included in the block is greatly different from a change in the normal deviation values of the pixels in the block when a lesion region is not included in the block.

FIGS. 4(a) and 4(b) are views showing changes in the normal deviation values of the pixels in the block for area A1 and area A2, respectively.

FIG. 4(a) shows a change in the normal deviation values of the pixels in the block for area A1 shown in FIG. 3. It can be seen that a change in the normal deviation values is not great and is almost uniform, whereby there is a high possibility of a lesion region not being present in the block.

FIG. 4(b) shows a change in the normal deviation values of the pixels in the block for area A2 shown in FIG. 3. It can be seen that a change in the normal deviation values remains almost uniform and that the normal deviation values are abruptly greatly changed in part f.

The appearance of a part in which a change in the normal deviation values is great, like part f, means that there is a high possibility of a lesion region being present in the part.

Consequently, it is necessary for the part in the block, in which the normal deviation values of the pixels are different from the average value by a predetermined level or more, to be distinguished from the other parts in the block such that a lesion region can be easily detected. Here, the part in the block, in which the normal deviation values of the pixels is different from the average value by a predetermined level or more is the mass described above.

In the present invention, while scanning the raw image 102 shown in FIG. 3 in units of a block PB, the mass extraction unit of the controller uniformly displays the pixels having normal deviation values lower than the threshold value as white and displays pixels having normal deviation values higher than the threshold value as black to create a binary image in which pixels having normal deviation values lower than the threshold value and pixels having normal deviation values higher than the threshold value are distinguished from each other.

FIG. 5(a) is a view showing an example of a binary image 104 created as described above, and FIG. 5(a) is an enlarged view showing a mass M in the binary image 104.

When a binary image is created from the raw image based on a predetermined threshold value for the normal deviation values, as shown in FIG. 5(a), a dark lump clearly appears in the image. The dark lump is a mass M.

There is a high possibility of a lesion position being included in the mass M in the binary image 104 shown in FIG. 5(a).

If the threshold value is set higher, the size of the mass M is smaller. If the threshold value is set lower, the size of the mass M is larger. If the size of the mass M is too small, there is a lower possibility of finding a pore in the mass. If the size of the mass M is too large, there is a higher possibility of finding a pore in the mass. However, there is also a higher possibility of a pore being falsely detected. Consequently, it is necessary to set an appropriate threshold value such that a mass of an appropriate size can be extracted.

By setting the threshold value in the manner described above, the same device may be used for all people having different skin colors.

For example, if a specific threshold value is set for people having yellow skin, a value lower than the specific threshold value may be set for people having black skin, and a value higher than the specific threshold value may be set for people having white skin. In this way, the same device may be used for all people having different skin colors.

In addition, since people having the same skin color may have somewhat different detection results depending on the skin tone of the people, the device may be configured such that the operator can manually minutely adjust the threshold value such that a lesion position can be very precisely detected depending on the professional skills of the operator.

Extraction of the mass corresponds to steps S120 and S130 in the flowchart of FIG. 2.

As shown in FIG. 5(b), however, the mass M in the binary image 104 may have various shapes. In order to more easily find a pore, i.e. a lesion position, in the mass, therefore, it may be necessary to set a simplified region including the mass. The simplified region may have various shapes, such as a quadrangular shape, a circular shape, and a polygonal shape. Preferably, the region is set to have a quadrangular shape.

FIG. 6 is a view showing a process of setting a simplified region including a mass as described above.

As shown in FIG. 6(a), a reference point Pc is set for a mass M, pixels are scanned from the reference point Pc in a predetermined direction, and a scan point Ps is set at a point of which the pixel value starts to vary, i.e. a point on the outline of the mass M.

Here, the reference point Pc may be an arbitrary point in the mass M or the average position or the center of gravity of the pixels constituting the mass M.

When the scan point Ps is set at the outline of the mass M, as described above, information about x-axis and y-axis coordinates of every position while the scan point Ps is moved along the outline of the mass M, as shown in FIG. 6(b), and the maximum and the minimum of the x-axis coordinate value and the y-axis coordinate value are continuously updated.

In this way, the scan point Ps is moved along the outline of the mass M.

When the scan point Ps is returned to the original position thereof, the maximum and the minimum of the x-axis coordinate value and the maximum and the minimum of the y-axis coordinate value of the mass M are set.

Here, the maximum x-axis coordinate value is denoted by x_max, the maximum y-axis coordinate value is denoted by y_max, the minimum x-axis coordinate value is denoted by x_min, and the minimum y-axis coordinate value is denoted by y_min.

As shown in FIG. 6(c), two points P1 and P2 for setting a region including a mass are set using the maximum and the minimum of the each coordinate value set as described above. Here, P1 and P2 are defined as follows.

$$P1(x\_min, y\_min)$$

$$P2(x\_max, y\_max)$$

P1 and P2 will be referred to as a first set point and a second set point, respectively, and a quadrangular region defined by the first set point and the second set point will be referred to as a "mass region."

When the first set point and the second set point are defined, as described above, the mass region may be set. When the region of the raw image corresponding to the mass region is analyzed, a lesion position may be detected.

Setting of the mass region corresponds to step S140 in the flowchart of FIG. 2.

FIG. 6(*c*) shows the case in which the mass region is defined as a quadrangular shape. However, the mass region is not necessarily defined as a quadrangular shape.

For example, the largest distance from one point to the other point of the mass may be calculated, and a circular region having the calculated distance as the diameter may be set as the mass region.

Meanwhile, when the mass region is set, as described above, the pixels in the set mass region Rm in the raw image 102 may be analyzed to detect a lesion position, as shown in FIG. 7(*a*).

A further description will be given hereinafter with reference to the elements shown in FIG. 1. When the mass extraction unit of the controller extracts a mass and sets a mass region from the mass, as shown in FIG. 6, the lesion position detection unit of the controller checks pixels in the region of the raw image 102 corresponding to the set mass region to detect a lesion position.

In order to detect a lesion position, as shown in FIG. 7(*a*), pixels in each mass region Rm are scanned one by one to check the brightness value of each pixel or to check the normal deviation value of each pixel.

As shown in FIG. 7(*a*), there is a dark part in each mass region Rm, and the dark part is a lesion position. Consequently, the lesion position detection unit may check the brightness values of the pixels in the mass region Rm to calculate the minimum brightness value. In addition, the lesion position detection unit may find pixels having brightness values within a predetermined range that is approximate to the minimum brightness value based on the calculated minimum brightness value to detect a pixel group corresponding to a lesion region. The part having the lowest brightness value in the detected pixel group may be detected as a lesion position.

In this way, it is possible to detect a lesion position using a method of checking brightness values. In addition, it is possible to calculate the normal deviation value of each pixel in the mass region Rm (i.e. the normal deviation value of the average value of all pixels in the mass region) and to detect a lesion position using the normal deviation value. This corresponds to step S150 in the flowchart of FIG. 2.

That is, the normal deviation values of the respective pixels in the region of the raw image 120 corresponding to the mass region Rm are calculated, and the position having the maximum normal deviation value is detected. The detected position is a lesion position. The position having the maximum normal deviation value may be one pixel or a plurality of pixels.

The result in which the position having the maximum normal deviation value in each mass region is detected as a lesion position as described above is shown in FIG. 7(*b*). FIG. 7(*b*) shows an image in which the position having the maximum normal deviation value as described above is detected and displayed as a lesion position LP.

In many cases, the position having the maximum normal deviation value is detected as a lesion position as described above, whereby detection is accurately performed. However, a plurality of positions having the maximum normal deviation value may be present in a specific mass region.

If a plurality of positions having the maximum normal deviation value is present in a specific mass region even though all settings are performed such that only one lesion position is detected in one mass region, this means that a plurality of positions having the maximum normal deviation value is detected due to noise in the image.

The present invention proposes a method of effectively detecting a lesion position even when a plurality of positions having the maximum normal deviation value is detected in a mass region as described above.

Cases in each of which a plurality of positions having the maximum normal deviation value is detected in a mass region as described above will be described with reference to FIGS. 8(*a*) to 8(*e*).

FIGS. 8(*a*) to 8(*c*) shows the case in which the same position is repeatedly detected or two positions that may be regarded as almost the same position are detected.

In the case in which a plurality of positions having the maximum normal deviation value is detected in a mass region, the Euclidean distance to all pixels corresponding to the detected positions is calculated.

A method of calculating the Euclidean distance is well known, and therefore a description thereof will be omitted.

When the calculated Euclidean distance to the positions is 0 or approximates 0, the detected positions may be regarded as the same position. This case is shown in FIGS. 8(*a*), 8(*b*), and 8(*c*).

In the case in which the Euclidean distance to the positions is 0 or approximates 0 and is less than a predetermined value, therefore, the lesion position detection unit of the present invention selects one of the detected positions and detects the selected position as a lesion position.

However, in the case in which the Euclidean distance to the positions is greater than the predetermined value, i.e. in the case in which the positions are spaced apart from each other by a predetermined distance, it is not possible to select one of the detected positions, and it is necessary to perform a process of checking and detecting a true lesion position from the positions.

FIGS. 8(*d*) and 8(*e*) show the case in which the detected positions are spaced apart from each other by a predetermined distance. The case shown in FIGS. 8(*d*) and 8(*e*) may occur due to noise in the image.

In the above case, it is necessary to perform an additional process of detecting a true lesion position, which will be described with reference to FIG. 9. FIGS. 9(*a*) and 9(*b*) show pixels in one mass region. It is assumed that if the color of each pixel is darker, the pixel has a larger normal deviation value.

It is assumed that two positions LP1 and LP2 have been detected in a specific mass region Rm, as shown in FIG. 9(*a*).

Since the positions LP1 and LP2 are spaced apart from each other by a predetermined distance, it is necessary to perform an additional process of checking and detecting which is a true lesion position.

In the above case, the lesion position detection unit of the present invention detects pixels in the mass region Rm having normal deviation values greater than a predetermined threshold value. Here, the threshold value may be the same as the threshold value used to extract the mass as shown in FIG. 5 or another appropriate value.

It is assumed that pixels having normal deviation values greater than the threshold value have been detected as an area a1, an area a2, and an area a3, as shown in FIG. 9(*b*).

In almost all cases, as previously described, a lesion position in a mass region is made up of a group of pixels that have very low brightness values, i.e. are dark. The number of pixels constituting the pixel group may be set in advance.

Consequently, the number of pixels constituting the pixel group, by which a lesion position is detected as described above, may be set in advance, and a pixel group having the predetermined number of pixels may be detected among pixels in the mass region Rm having normal deviation values greater than the threshold value.

In the example shown in FIG. 9(b), the area a3 may be excluded, since the area a3 has a very small number of pixels (it is assumed that the predetermined number of pixels is greater than 3). Consequently, one of the area a1 and the area a2 is a pixel group having a lesion position.

In general, when a pixel group having a predetermined number of pixels as described above is detected, a position may be detected, and the detected position may be a lesion position. In the example shown in FIG. 9(b), it is assumed that the area a1 and the area a2 form pixel groups.

In the case in which a plurality of pixel groups is detected, the maximum normal deviation values of the pixel groups are calculated and compared. One of the pixel groups having the larger maximum normal deviation value is a pixel group having a lesion position.

In the example shown in FIG. 9(b), therefore, the area a1 may be finally determined to be a pixel group having a lesion position, and the position LP1 may be detected as a final lesion position.

Meanwhile, it is possible to detect a lesion position using the Mahalanobis distance, instead of using the Euclidean distance for data as described above.

The Mahalanobis distance is a distance indicating a degree of proximity to a group of data gathered based on a covariance of data.

When only data (i.e. pixels) in the mass region Rm shown in FIG. 9(b), the normal deviation values of which are higher than the threshold value, are extracted and covariance of the extracted data is calculated, it is assumed that information about covariance is provided as shown in FIG. 10.

In the covariance graph shown in FIG. 10, the area a1 shown in FIG. 9(b), i.e. a pixel group having a lesion position, has the highest degree of data concentration.

When the Mahalanobis distance between arbitrary points p and b1 and the Mahalanobis distance between arbitrary points p and b2 are calculated (the Euclidean between the points p and b1 and the Euclidean distance between the points p and b2 are the same), the distance between the points p and b1, which is closer to the pixel group, is shorter than the distance between the points p and b2.

That is, since the points b1 and b2 are spaced apart from the point p by the same distance but point b1 is closer to the pixel group, the Mahalanobis distance between the points p and b1 is shorter than the Mahalanobis distance between arbitrary points p and b2.

Consequently, a predetermined value may be set for the Mahalanobis distance in advance, and data having Mahalanobis distance values shorter than the predetermined value may be selected to detect a pixel group having a lesion position. That is, in FIG. 9(b), the area a1 may be detected using the Mahalanobis distance information, and the lesion position LP1 may be detected therefrom.

As described above, the present invention provides a method of extracting a mass having a lesion position using an image of the skin of a patient, setting a mass region, and precisely detecting a lesion position from the region of a raw image corresponding to the mass region, thereby accurately treating only the lesion position on the skin of the patient without affecting the other regions of the skin of the patient. Consequently, it is possible to prevent the occurrence of serious side effects, such as skin burns and spots, on the treated region during the treatment process.

INDUSTRIAL APPLICABILITY

A light treatment device using lesion image analysis according to the present invention and a method of detecting a lesion position through lesion image analysis for use therein are applicable to industries related to medical instruments that are capable of analyzing an image of the skin of a patient and automatically removing hairs, freckles, blemishes, flecks, etc. and treating various kinds of skin diseases using a specific kind of light, such as a laser, and medical treatment devices for skin care.

The invention claimed is:

1. A method of detecting a lesion position through lesion image analysis for use in a light treatment device for treating a lesion region, the method comprising:
   acquiring an image of a partial region of a skin of a patient by a camera; and
   detecting a lesion position by a controller of the light treatment device, the controller configured to:
      normalize the acquired image with respect to light based on a predetermined parameter;
      set a plurality of blocks of a predetermined size in the normalized image, scan the normalized image by the set blocks, and calculate normal deviation values of pixels in each of the blocks;
      create a binary image in which pixels in each block having normal deviation values lower than a predetermined threshold value and pixels in each block having normal deviation values higher than the predetermined threshold value are distinguished from each other so that a mass which is a region including the lesion position clearly appears in the binary image;
      extract the mass from the binary image;
      set a mass region including the extracted mass in the binary image;
      calculate a normal deviation value of pixels in a region of the acquired image or the normalized image corresponding to the set mass region; and
      detect a position at which the calculated normal deviation value is a maximum value as the lesion position.

2. A method of detecting a lesion position through lesion image analysis for use in a light treatment device for treating a lesion region, the method comprising:
   acquiring an image of a partial region of a skin of a patient by a camera; and
   detecting a lesion position by a controller of the light treatment device, the controller configure to:
      normalize the acquired image with respect to light based on a predetermined parameter;
      set a plurality of blocks of a predetermined size in the normalized image, scan the normalized image by the set blocks, and calculate normal deviation values of pixels in each of the blocks;
      create a binary image in which pixels in each block having normal deviation values lower than a predetermined threshold value and pixels in each block having normal deviation values higher than the predetermined threshold value are distinguished from each other so that a mass which is a region including the lesion position clearly appears in the binary image;
      extract the mass from the binary image;
      set a mass region including the extracted mass in the binary image;
      detect a minimum brightness value of each pixel in a region of the acquired image or the normalized image corresponding to the set mass region; and
      detect a pixel group having a predetermined range of brightness values based on the detected minimum brightness value as the lesion region.

3. The method according to claim 2, wherein the step of detecting the pixel group comprises, in a case in which a plurality of pixel groups is detected, detecting one of the pixel groups having a highest deviation with respect to an average of brightness values of all pixels and detecting a position in the detected pixel group at which the brightness value of the pixel is a minimum as the lesion position.

4. The method according to claim 1, wherein the step of detecting the position comprises,
   detecting the lesion position through different processes in a case in which a single position at which the calculated normal deviation value is a maximum value is detected and in a case in which a plurality of positions at each of which the calculated normal deviation is a maximum are detected.

5. The method according to claim 4, comprising:
   in the case in which the plurality of positions are detected, calculating a Euclidean distance between points at all of the detected positions; and
   in a case in which the calculated Euclidean distance is less than a predetermined value, selecting one of the detected positions and determining the selected position to be the lesion position.

6. The method according to claim 4, comprising:
   in the case in which the plurality of positions are detected, calculating a Euclidean distance between points at all of the detected positions; and
   in a case in which the calculated Euclidean distance is greater than a predetermined value, detecting pixels having normal deviation values higher than a threshold value set in advance for the normal deviation value calculated at the step of calculating the normal deviation value of each pixel; and
   calculating the Euclidean distance between the detected pixels to detect a pixel group having pixels gathered in a predetermined value or lower and detecting a position in the detected pixel group at which the normal deviation value is a maximum as the lesion position.

7. The method according to claim 1, further comprising:
   calculating a covariance for positions of the detected pixels and calculating a Mahalanobis distance between points based on the calculated covariance; and
   detecting a pixel group having the calculated Mahalanobis distance less than a predetermined value as the lesion position.

* * * * *